(12) United States Patent
Singh et al.

(10) Patent No.: US 8,784,879 B2
(45) Date of Patent: Jul. 22, 2014

(54) TRANSDERMAL ADMINISTRATION OF TAMSULOSIN

(75) Inventors: Parminder Singh, Union City, CA (US); Eun Soo Lee, Redwood City, CA (US); Amit K. Jain, Milpitas, CA (US)

(73) Assignee: Corium International, Inc., Menlo Park, CA (US)

(*) Notice: Subject to any disclaimer, the term of this patent is extended or adjusted under 35 U.S.C. 154(b) by 266 days.

(21) Appl. No.: 12/687,586

(22) Filed: Jan. 14, 2010

(65) Prior Publication Data

US 2010/0291186 A1 Nov. 18, 2010

Related U.S. Application Data

(60) Provisional application No. 61/144,728, filed on Jan. 14, 2009.

(51) Int. Cl.
*A61K 9/70* (2006.01)
*A61F 13/02* (2006.01)
*A61K 9/00* (2006.01)
*A61K 31/18* (2006.01)
*A61K 31/75* (2006.01)
*C07C 311/37* (2006.01)

(52) U.S. Cl.
USPC ............ 424/449; 514/603; 564/86; 564/89

(58) Field of Classification Search
USPC ........................... 424/449; 514/603
See application file for complete search history.

(56) References Cited

U.S. PATENT DOCUMENTS

| | | | |
|---|---|---|---|
| 2,561,071 | A | 7/1951 | Prisk |
| 2,579,403 | A | 12/1951 | Slomowitz et al. |
| 3,150,977 | A | 9/1964 | Hart et al. |
| 3,689,439 | A | 9/1972 | Field et al. |
| 3,721,657 | A | 3/1973 | Seiderman |
| 3,749,755 | A | 7/1973 | Bronstart et al. |
| 3,852,228 | A | 12/1974 | Brothers |

(Continued)

FOREIGN PATENT DOCUMENTS

| | | |
|---|---|---|
| CA | 2520986 | 4/2000 |
| CA | 2402021 | 9/2001 |

(Continued)

OTHER PUBLICATIONS

U.S. Appl. No. 11/150,811, filed Jun. 10, 2005, Feldstein, et al.

(Continued)

*Primary Examiner* — Jane C Oswecki
(74) *Attorney, Agent, or Firm* — Judy M. Mohr; Susan J. Myers Fitch; McDermott Will & Emery LLP

(57) ABSTRACT

In an aspect of the invention, a composition for making a patch for the transdermal delivery of tamsulosin is provided. The composition comprises (a) at least about 1 wt % tamsulosin or a pharmaceutically acceptable salt of tamsulosin, (b) at least about 40 wt % polyisobutylene adhesive or hydrophobic synthetic rubber adhesive, (c) about 1-20 wt % of an aprotic solvent in which tamsulosin dissolves readily, (d) about 1-20 wt % of an unsaturated fatty acid or an alpha-hydroxy acid or a mixture of unsaturated fatty acids or alpha-hydroxy acids or of both unsaturated fatty acids and alpha-hydroxy acids, (e) a lipophilic permeation enhancer, and (f) a matrix modifier.

40 Claims, 7 Drawing Sheets

(56) References Cited

U.S. PATENT DOCUMENTS

| | | | |
|---|---|---|---|
| 3,957,605 A | 5/1976 | Assarsson et al. |
| 3,993,551 A | 11/1976 | Assarsson et al. |
| 3,996,934 A | 12/1976 | Zaffaroni |
| 4,091,090 A | 5/1978 | Sipos |
| 4,093,673 A | 6/1978 | Chang et al. |
| 4,160,020 A | 7/1979 | Ayer et al. |
| 4,231,369 A | 11/1980 | Sorensen et al. |
| 4,277,580 A | 7/1981 | Allen et al. |
| 4,325,851 A | 4/1982 | Colon et al. |
| 4,346,709 A | 8/1982 | Schmitt et al. |
| 4,367,732 A | 1/1983 | Poulsen et al. |
| 4,492,685 A | 1/1985 | Keith et al. |
| 4,529,601 A | 7/1985 | Broberg et al. |
| 4,552,751 A | 11/1985 | Inaba et al. |
| 4,557,934 A | 12/1985 | Cooper |
| 4,562,060 A | 12/1985 | Broberg et al. |
| 4,568,343 A | 2/1986 | Leeper et al. |
| 4,587,289 A | 5/1986 | Comert et al. |
| 4,593,053 A | 6/1986 | Jevne et al. |
| 4,624,665 A | 11/1986 | Nuwayser |
| 4,699,146 A | 10/1987 | Sieverding |
| 4,713,243 A | 12/1987 | Schiraldi et al. |
| 4,743,249 A | 5/1988 | Loveland |
| 4,750,482 A | 6/1988 | Sieverding |
| 4,771,105 A | 9/1988 | Shirai et al. |
| 4,849,224 A | 7/1989 | Chang et al. |
| 4,863,738 A | 9/1989 | Taskovich |
| 4,863,970 A | 9/1989 | Patel et al. |
| 4,867,748 A | 9/1989 | Samuelsen |
| 4,871,536 A | 10/1989 | Arraudeau et al. |
| 4,873,299 A | 10/1989 | Nawoakosky et al. |
| 4,877,628 A | 10/1989 | Stypula |
| 4,904,247 A | 2/1990 | Therriault et al. |
| 4,906,169 A | 3/1990 | Chien et al. |
| 4,927,408 A | 5/1990 | Haak et al. |
| 4,945,084 A | 7/1990 | Packman |
| 4,953,053 A | 8/1990 | Pratt |
| 4,973,468 A | 11/1990 | Chiang et al. |
| 4,983,395 A | 1/1991 | Chang et al. |
| 5,023,084 A | 6/1991 | Chien et al. |
| 5,053,227 A | 10/1991 | Chiang et al. |
| 5,057,500 A | 10/1991 | Thornfelt |
| 5,073,381 A | 12/1991 | Ivan et al. |
| 5,102,662 A | 4/1992 | Gallagher |
| 5,125,894 A | 6/1992 | Phipps et al. |
| 5,133,970 A | 7/1992 | Petereit et al. |
| 5,141,750 A | 8/1992 | Lee et al. |
| 5,173,302 A | 12/1992 | Holmblad et al. |
| 5,183,901 A | 2/1993 | Login et al. |
| 5,196,405 A | 3/1993 | Packman |
| 5,200,190 A | 4/1993 | Azuma et al. |
| 5,206,385 A | 4/1993 | Login et al. |
| 5,224,928 A | 7/1993 | Sibalis et al. |
| 5,232,702 A | 8/1993 | Pfister et al. |
| 5,234,690 A | 8/1993 | Chiang et al. |
| 5,234,957 A | 8/1993 | Mantelle |
| 5,240,995 A | 8/1993 | Gyory et al. |
| 5,254,346 A | 10/1993 | Tucker et al. |
| 5,270,358 A | 12/1993 | Asmus |
| 5,276,079 A | 1/1994 | Duan et al. |
| 5,296,512 A | 3/1994 | Beier et al. |
| 5,300,291 A | 4/1994 | Sablotsky et al. |
| 5,310,563 A | 5/1994 | Curtis et al. |
| 5,322,689 A | 6/1994 | Hughes et al. |
| 5,326,685 A | 7/1994 | Gaglio et al. |
| 5,332,576 A | 7/1994 | Mantelle |
| 5,338,490 A | 8/1994 | Dietz et al. |
| 5,342,623 A | 8/1994 | Enscore et al. |
| 5,344,394 A | 9/1994 | Gyory et al. |
| 5,354,823 A | 10/1994 | Tseng et al. |
| 5,362,420 A | 11/1994 | Itoh et al. |
| 5,376,377 A | 12/1994 | Gale et al. |
| 5,422,119 A | 6/1995 | Casper |
| 5,438,076 A | 8/1995 | Friedman et al. |
| 5,446,070 A | 8/1995 | Mantelle |
| 5,456,745 A | 10/1995 | Roreger et al. |
| 5,462,743 A | 10/1995 | Turner et al. |
| 5,462,745 A | 10/1995 | Enscore et al. |
| 5,492,943 A | 2/1996 | Stempel |
| 5,508,024 A | 4/1996 | Tranner |
| 5,508,367 A | 4/1996 | Zajaczkowski |
| 5,527,271 A | 6/1996 | Shah et al. |
| 5,543,148 A | 8/1996 | Lapidus |
| 5,563,153 A | 10/1996 | Mueller et al. |
| 5,575,654 A | 11/1996 | Fontenot |
| 5,593,686 A | 1/1997 | Kissel et al. |
| 5,594,068 A | 1/1997 | Buchanan et al. |
| 5,599,373 A | 2/1997 | Zanuccoli |
| 5,614,178 A | 3/1997 | Bloon et al. |
| 5,631,267 A | 5/1997 | Gliech et al. |
| 5,633,010 A | 5/1997 | Chen |
| 5,641,504 A | 6/1997 | Lee et al. |
| 5,641,507 A | 6/1997 | DeVillez |
| 5,643,187 A | 7/1997 | Naestoft et al. |
| 5,645,062 A | 7/1997 | Anderson et al. |
| 5,645,855 A | 7/1997 | Lorenz |
| 5,656,286 A | 8/1997 | Miranda et al. |
| 5,660,178 A | 8/1997 | Kantner et al. |
| 5,662,925 A | 9/1997 | Ebert et al. |
| 5,663,010 A | 9/1997 | Stocchiero |
| 5,674,561 A | 10/1997 | Dietz et al. |
| 5,700,478 A | 12/1997 | Biegajski et al. |
| 5,702,721 A | 12/1997 | Horstmann et al. |
| 5,718,187 A | 2/1998 | Pollock et al. |
| 5,718,886 A | 2/1998 | Pellico |
| 5,719,197 A | 2/1998 | Kanios et al. |
| 5,723,145 A | 3/1998 | Shikinami et al. |
| 5,725,876 A | 3/1998 | Mantelle et al. |
| 5,726,250 A | 3/1998 | Zajaczkowski |
| 5,730,999 A | 3/1998 | Lehmann et al. |
| 5,744,155 A | 4/1998 | Freidman et al. |
| 5,762,956 A | 6/1998 | Chien |
| 5,770,220 A | 6/1998 | Meconi et al. |
| 5,773,490 A | 6/1998 | Shikinami et al. |
| 5,780,050 A | 7/1998 | Jain et al. |
| 5,785,527 A | 7/1998 | Jensen et al. |
| 5,785,976 A | 7/1998 | Westesen et al. |
| 5,788,983 A | 8/1998 | Chien et al. |
| 5,800,832 A | 9/1998 | Tapolsky et al. |
| 5,804,611 A | 9/1998 | Takoh et al. |
| 5,827,213 A | 10/1998 | Jensen |
| 5,827,525 A | 10/1998 | Liao et al. |
| 5,830,932 A | 11/1998 | Kay |
| 5,837,713 A | 11/1998 | Gliech et al. |
| 5,843,472 A | 12/1998 | Ma et al. |
| 5,846,558 A | 12/1998 | Nielsen et al. |
| 5,851,549 A | 12/1998 | Svec |
| 5,853,755 A | 12/1998 | Foldvari |
| 5,858,332 A | 1/1999 | Jensen et al. |
| 5,858,410 A | 1/1999 | Muller et al. |
| 5,863,662 A | 1/1999 | Hornby et al. |
| 5,876,746 A | 3/1999 | Jona et al. |
| 5,879,691 A | 3/1999 | Sagel et al. |
| 5,879,701 A * | 3/1999 | Audett et al. ................ 424/448 |
| 5,891,453 A | 4/1999 | Sagel et al. |
| 5,894,017 A | 4/1999 | Sagel et al. |
| 5,900,249 A | 5/1999 | Smith |
| 5,902,598 A | 5/1999 | Chen et al. |
| 5,911,980 A | 6/1999 | Samour et al. |
| 5,912,271 A | 6/1999 | Brodine et al. |
| 5,916,587 A | 6/1999 | Min et al. |
| 5,942,543 A | 8/1999 | Ernst |
| 5,945,032 A | 8/1999 | Breitenbach et al. |
| 5,945,457 A | 8/1999 | Plate et al. |
| 5,948,416 A | 9/1999 | Wagner et al. |
| 5,948,430 A | 9/1999 | Zerbe et al. |
| 5,948,433 A | 9/1999 | Burton et al. |
| 5,958,379 A | 9/1999 | Regenold et al. |
| 5,958,446 A | 9/1999 | Miranda et al. |
| 5,958,984 A | 9/1999 | Devillez |
| 5,962,011 A | 10/1999 | DeVillez |
| 5,972,377 A | 10/1999 | Jona et al. |
| 5,976,565 A | 11/1999 | Fotinos |
| 5,985,311 A | 11/1999 | Cordes et al. |

(56) References Cited

U.S. PATENT DOCUMENTS

| | | |
|---|---|---|
| 5,985,860 A | 11/1999 | Toppo |
| 5,985,990 A | 11/1999 | Kantner et al. |
| 5,989,569 A | 11/1999 | Dirksing et al. |
| 5,990,179 A | 11/1999 | Gyori et al. |
| 5,993,836 A | 11/1999 | Castillo |
| 5,993,849 A | 11/1999 | Assmus et al. |
| 5,997,886 A | 12/1999 | Peffly et al. |
| 6,004,566 A | 12/1999 | Freidman et al. |
| 6,004,578 A | 12/1999 | Lee et al. |
| 6,007,837 A | 12/1999 | Enscore et al. |
| 6,024,976 A | 2/2000 | Miranda et al. |
| 6,045,811 A | 4/2000 | Dirksing et al. |
| 6,051,609 A | 4/2000 | Yu et al. |
| 6,063,399 A | 5/2000 | Assmus et al. |
| 6,068,650 A | 5/2000 | Hofmann et al. |
| 6,072,100 A | 6/2000 | Mooney et al. |
| 6,075,626 A | 6/2000 | Mizutani et al. |
| 6,083,421 A | 7/2000 | Huang et al. |
| 6,093,328 A | 7/2000 | Santina |
| 6,096,328 A | 8/2000 | Sagel et al. |
| 6,135,126 A | 10/2000 | Joshi |
| 6,142,939 A | 11/2000 | Eppstein et al. |
| 6,146,654 A | 11/2000 | Kubo |
| 6,153,215 A | 11/2000 | Samuelsen et al. |
| 6,162,456 A | 12/2000 | Dunbar et al. |
| 6,165,499 A | 12/2000 | Kleinsorgen et al. |
| 6,177,096 B1 | 1/2001 | Zerbe et al. |
| 6,193,993 B1 | 2/2001 | Murahashi et al. |
| 6,197,331 B1 | 3/2001 | Lerner et al. |
| 6,201,164 B1 | 3/2001 | Wulff et al. |
| 6,212,671 B1 | 4/2001 | Kanehira et al. |
| 6,221,341 B1 | 4/2001 | Montgomery |
| 6,221,383 B1 | 4/2001 | Miranda et al. |
| 6,231,885 B1 | 5/2001 | Carrarra |
| 6,248,363 B1 | 6/2001 | Patel et al. |
| 6,264,981 B1 | 7/2001 | Zhang et al. |
| 6,270,792 B1 | 8/2001 | Guillemet et al. |
| 6,275,728 B1 | 8/2001 | Venkatraman et al. |
| 6,306,370 B1 | 10/2001 | Jensen et al. |
| 6,312,666 B1 | 11/2001 | Oxman et al. |
| 6,312,670 B1 | 11/2001 | Montgomery |
| 6,316,022 B1 | 11/2001 | Mantelle et al. |
| 6,322,774 B1 | 11/2001 | Jensen et al. |
| 6,329,472 B1 | 12/2001 | Kim et al. |
| 6,368,576 B1 | 4/2002 | Jensen et al. |
| 6,419,905 B1 | 7/2002 | Alvarez Hernandez |
| 6,419,906 B1 | 7/2002 | Xu et al. |
| 6,451,240 B1 | 9/2002 | Sherman et al. |
| 6,451,777 B1 | 9/2002 | Bradbury et al. |
| 6,461,636 B1 | 10/2002 | Arth et al. |
| 6,488,913 B2 | 12/2002 | Orlowski et al. |
| 6,517,350 B2 | 2/2003 | Diasti et al. |
| 6,552,147 B2 | 4/2003 | Parker et al. |
| 6,558,654 B2 | 5/2003 | McLaughlin |
| 6,562,363 B1 | 5/2003 | Mantelle et al. |
| 6,576,712 B2 | 6/2003 | Feldstein et al. |
| 6,585,997 B2 | 7/2003 | Moro et al. |
| 6,591,124 B2 | 7/2003 | Sherman et al. |
| 6,596,298 B2 | 7/2003 | Leung et al. |
| 6,602,912 B2 | 8/2003 | Hsu et al. |
| 6,611,706 B2 | 8/2003 | Avrahami et al. |
| 6,638,528 B1 | 10/2003 | Kanios |
| 6,656,493 B2 | 12/2003 | Dzija |
| 6,667,410 B2 | 12/2003 | Manbus et al. |
| 6,673,363 B2 | 1/2004 | Luo et al. |
| 6,682,721 B2 | 1/2004 | Kim et al. |
| 6,689,344 B2 | 2/2004 | Chang et al. |
| 6,696,459 B1 | 2/2004 | Jones et al. |
| 6,708,060 B1 | 3/2004 | Avrahami et al. |
| 6,709,671 B2 | 3/2004 | Zerbe et al. |
| 6,711,435 B2 | 3/2004 | Avrahami |
| 6,714,497 B2 | 3/2004 | Yeo et al. |
| 6,750,291 B2 | 6/2004 | Kim et al. |
| 6,759,030 B2 | 7/2004 | Kosti |
| 6,762,202 B2 | 7/2004 | Marek et al. |
| 6,780,401 B2 | 8/2004 | Kim et al. |
| 6,783,769 B1 | 8/2004 | Arth et al. |
| 6,803,420 B2 | 10/2004 | Cleary et al. |
| 6,805,874 B1 | 10/2004 | Lutz et al. |
| 6,806,308 B2 | 10/2004 | Zajac |
| 6,884,833 B2 | 4/2005 | Cheang et al. |
| 6,946,142 B2 | 9/2005 | Chang et al. |
| 6,962,691 B1 | 11/2005 | Lulla et al. |
| 7,078,359 B2 | 7/2006 | Stepanian et al. |
| 7,112,713 B2 | 9/2006 | Sceusa |
| 7,122,199 B2 | 10/2006 | Sagel et al. |
| 7,138,458 B2 | 11/2006 | Cleary et al. |
| 7,217,853 B2 | 5/2007 | Kulichikhin et al. |
| 7,323,161 B2 | 1/2008 | Choi et al. |
| 7,384,650 B2 | 6/2008 | Chien |
| 7,456,331 B2 | 11/2008 | Kulichikhin et al. |
| 7,744,918 B2 | 6/2010 | Yamaguchi et al. |
| 8,206,738 B2 | 6/2012 | Singh et al. |
| 8,273,405 B2 | 9/2012 | Feldstein et al. |
| 8,481,059 B2 | 7/2013 | Cleary et al. |
| 8,481,071 B2 | 7/2013 | Singh et al. |
| 2001/0006677 A1 | 7/2001 | Mcginty et al. |
| 2001/0021374 A1 | 9/2001 | Montgomery |
| 2001/0046471 A1 | 11/2001 | Marek et al. |
| 2002/0004190 A1 | 1/2002 | Diasti et al. |
| 2002/0009420 A1 | 1/2002 | McLaughlin |
| 2002/0048602 A1 | 4/2002 | Flore et al. |
| 2002/0076487 A1 | 6/2002 | Zajac |
| 2002/0106335 A1 | 8/2002 | Orlowski et al. |
| 2002/0131990 A1 | 9/2002 | Barkalow et al. |
| 2002/0197284 A1 | 12/2002 | Luo et al. |
| 2003/0035841 A1 | 2/2003 | Dzija |
| 2003/0055190 A1 | 3/2003 | Parker et al. |
| 2003/0068376 A1 | 4/2003 | Chen et al. |
| 2003/0100654 A1 | 5/2003 | Cheang et al. |
| 2003/0101507 A1 | 6/2003 | Cleary et al. |
| 2003/0103427 A1 | 6/2003 | Yeo et al. |
| 2003/0104041 A1* | 6/2003 | Hsu et al. .................. 424/449 |
| 2003/0152528 A1 | 8/2003 | Singh et al. |
| 2003/0152615 A1 | 8/2003 | Houze et al. |
| 2003/0170308 A1 | 9/2003 | Cleary et al. |
| 2003/0180229 A1 | 9/2003 | Kosti |
| 2003/0225356 A1 | 12/2003 | Kulichikhin et al. |
| 2003/0235549 A1 | 12/2003 | Singh et al. |
| 2004/0005277 A1 | 1/2004 | Willison et al. |
| 2004/0053901 A1 | 3/2004 | Chien |
| 2004/0105834 A1 | 6/2004 | Singh et al. |
| 2004/0136927 A1 | 7/2004 | Kim et al. |
| 2004/0166147 A1 | 8/2004 | Lundy et al. |
| 2004/0219111 A1 | 11/2004 | Kim et al. |
| 2004/0258723 A1 | 12/2004 | Singh et al. |
| 2005/0031554 A1 | 2/2005 | Kim et al. |
| 2005/0113510 A1 | 5/2005 | Feldstein et al. |
| 2005/0208110 A1 | 9/2005 | Singh et al. |
| 2005/0214727 A1 | 9/2005 | Stoianovici et al. |
| 2005/0215727 A1 | 9/2005 | Feldstein et al. |
| 2005/0228113 A1 | 10/2005 | Baumer et al. |
| 2005/0256223 A1 | 11/2005 | Kolb et al. |
| 2006/0034905 A1 | 2/2006 | Singh et al. |
| 2006/0110434 A1* | 5/2006 | Yamaguchi et al. .......... 424/448 |
| 2006/0168905 A1 | 8/2006 | Blanc et al. |
| 2006/0171906 A1 | 8/2006 | Singh et al. |
| 2006/0182788 A1 | 8/2006 | Singh et al. |
| 2006/0193793 A1 | 8/2006 | Kim et al. |
| 2006/0193794 A1 | 8/2006 | Kim et al. |
| 2008/0161492 A1 | 7/2008 | Cleary et al. |
| 2009/0155343 A1* | 6/2009 | Kawahara et al. ............ 424/449 |
| 2009/0258060 A1 | 10/2009 | Cleary et al. |
| 2012/0027695 A1 | 2/2012 | Feldstein et al. |
| 2012/0237579 A1 | 9/2012 | Singh et al. |
| 2012/0321569 A1 | 12/2012 | Feldstein et al. |

FOREIGN PATENT DOCUMENTS

| | | |
|---|---|---|
| CA | 2451431 | 1/2003 |
| CA | 2506073 | 6/2004 |
| CA | 2579492 | 3/2006 |
| DE | 8509793 | 5/1985 |
| DE | 4219368 | 6/1992 |

(56) References Cited

FOREIGN PATENT DOCUMENTS

| | | |
|---|---|---|
| EP | 0184470 | 6/1986 |
| EP | 0303445 | 2/1989 |
| EP | 0364211 | 4/1990 |
| EP | 0371421 | 6/1990 |
| EP | 0511782 | 11/1992 |
| EP | 0516026 | 12/1992 |
| EP | 0545594 | 6/1993 |
| EP | 0581581 | 2/1994 |
| EP | 0672094 | 9/1995 |
| EP | 0737477 | 10/1996 |
| EP | 0838225 | 4/1998 |
| EP | 0848960 | 6/1998 |
| EP | 1066823 | 1/2001 |
| EP | 2005952 A1 | 12/2008 |
| GB | 1108837 | 4/1968 |
| JP | 58-162681 | 9/1983 |
| JP | 59-196817 | 11/1984 |
| JP | 01-151524 A | 6/1989 |
| JP | 03-066612 | 3/1991 |
| JP | 03-247334 | 5/1991 |
| JP | 03-275619 | 6/1991 |
| JP | 04-266818 | 9/1992 |
| JP | 06-100467 | 4/1994 |
| JP | 10-017448 | 1/1998 |
| JP | 2001-213768 A | 7/2001 |
| JP | 2002-029949 | 1/2002 |
| JP | 2002-145746 A | 5/2002 |
| KR | 20020045224 | 6/2002 |
| KR | 20030000299 | 1/2003 |
| KR | 20030000528 | 1/2003 |
| KR | 20030003969 | 1/2003 |
| KR | 20030003973 | 1/2003 |
| RU | 1459215 | 11/1995 |
| WO | WO 89/03859 | 5/1989 |
| WO | WO 90/07940 A1 | 7/1990 |
| WO | WO 93/02717 | 2/1993 |
| WO | WO 94/05340 | 3/1994 |
| WO | WO 96/19205 | 6/1996 |
| WO | WO 97/11676 | 4/1997 |
| WO | WO 99/11728 A1 | 3/1998 |
| WO | WO 98/20862 A1 | 5/1998 |
| WO | WO 98/26763 A1 | 6/1998 |
| WO | WO 98/37870 | 9/1998 |
| WO | WO 98/55044 | 12/1998 |
| WO | WO 99/17738 | 4/1999 |
| WO | WO 99/44678 | 9/1999 |
| WO | WO 99/47128 | 9/1999 |
| WO | WO 99/54422 | 10/1999 |
| WO | WO 99/55312 A2 | 11/1999 |
| WO | WO 00/16725 | 3/2000 |
| WO | WO 00/18365 A2 | 4/2000 |
| WO | WO 00/61120 A1 | 10/2000 |
| WO | WO 00/69421 | 11/2000 |
| WO | WO 01/01958 A1 | 1/2001 |
| WO | WO 01/07018 A1 | 2/2001 |
| WO | WO 01/26637 | 4/2001 |
| WO | WO 01/68045 | 9/2001 |
| WO | WO 01/87276 | 11/2001 |
| WO | WO 02/00182 A3 | 1/2002 |
| WO | WO 02/04570 | 1/2002 |
| WO | WO 02/43657 A2 | 6/2002 |
| WO | WO 02/087642 | 11/2002 |
| WO | WO 02/087645 | 11/2002 |
| WO | WO 02/089849 | 11/2002 |
| WO | WO 03/000216 | 1/2003 |
| WO | WO 03/011259 A1 | 2/2003 |
| WO | WO 03/089046 | 10/2003 |
| WO | WO 03/099344 | 12/2003 |
| WO | WO 03/101357 A1 | 12/2003 |
| WO | WO 2004/045569 | 6/2004 |
| WO | WO 2004/054638 | 7/2004 |
| WO | WO 2004/071323 | 8/2004 |
| WO | WO 2004/093786 | 11/2004 |
| WO | WO 2004/103201 | 12/2004 |
| WO | WO 2005/027768 | 3/2005 |
| WO | WO 2005/074894 A1 | 8/2005 |
| WO | WO 2006/017807 | 2/2006 |
| WO | WO 2006/029407 | 3/2006 |
| WO | WO 2006/069236 | 6/2006 |
| WO | WO 2006/074173 | 7/2006 |
| WO | WO 2006/081497 | 8/2006 |
| WO | WO 2006/124639 | 11/2006 |
| WO | WO 2007/119656 A1 | 10/2007 |
| WO | WO 2010/083035 | 7/2010 |

OTHER PUBLICATIONS

U.S. Appl. No. 12/687,586, filed Jan. 11, 2009, Singh, et al.

Aubin, et al., "Analysis of the glass transistion temperature of miscible polymer blends", Macromolecules, vol. 21, pp. 2945-2949, (1988).

Bairamov, et al., "Kinetic parameters of poly(N-vinyl pyrrolidone) spontaneous mixing with short-chain poly(ethylene glycol)", Polym. Mater. Sci. Eng., vol. 82, pp. 7-8, (2000).

Borodulina, et al. "Viscoelasticity of Pressure-sensitive adhesive and bioadhesive hydrogels under compressive load", Proceed. 24th Annual Meeting Adhesion Soc., pp. 147-149, (2001).

Chalykh, et al., "Effects of composition and hydration on adhesive properties of poly(N-vinyl pyrrolidone)-poly(ethylene glycol) hydrogels", Polym. Mater. Sci. Eng., vol. 81, pp. 456-457, (1999).

Chalykh, et al., "Fracture mechanics of poly(N-vinyl pyrrolidone)-poly(ethylene glycol) hydrogel adhesive joints," Polym. Mater. Sci. Eng., vol. 81, pp. 427-428, (1999).

Chalykh, et al., "Pressure-sensitive adhesion in the blends of poly(N-vinyl pyrrolidone) and poly(ethylene glycol) of disparate chain lengths," J. Adhesion, vol. 78, pp. 667-694, (2002).

Cleary, et. al., A new polymer blend adhesive with combined properties to adhere to either skin or mucosa for drug delivery, podium abstract, 30th Annual Meeting and Exposition of the Controlled Release Society, Glasgow, Scotland, Jul. 19-23, 2003, Abstract #123.

Database WPI Section Ch, Week 198451, Derwent Publicztions Ltd., London, GB; Class A96, AN 1984-315114 & JP 59196817 A (Sekisuki Chem Ind Co Ltd) Nov. 8, 1984 abstract.

Database WPI Section Ch, Week 199150, Derwent Publications Ltd., London, GB; Class A18, AN 1991-366353 & JP 03247334 A (Sumitomo Rubber Ind Ltd) Nov. 5, 1991 abstract.

Database WPI Section Ch, Week 199118, Derwent Publications Ltd., London, GB; Class A96, AN 1991-128478 & JP 03066612 A (Sato Pharm Co Ltd) Mar. 22, 1991 abstract.

Database WPI Section Ch, Week 199627, Derwent Publications Ltd., London, GB; Class A14, AN 1996-266746 & SU 1459215 A (A Med Cardiology Res Centre) Nov. 20, 1995 abstract.

Feldstein, et al., "A structure—property relationship and quantitative approach to the development of universal transdermal drug delivery system," NBC Risks, vol. 25, pp. 441-458, (1999).

Feldstein, et al., "Coherence of thermal transitions in poly(N-vinyl pyrrolidone)-poly(ethylene glycol) compatible blends: 1. Interrelations among the temperatures of melting, maximum cold crystalization rate and glass transition", Polymer, vol. 41, pp. 5327-5338, (2000).

Feldstein, et al., "Coherence of thermal transitions in poly(N-vinyl pyrrolidone)-poly(ethylene glycol) compatible blends: 2. The temperature of maximum cold crystalization rate versus glass transition", Polymer, vol. 41, pp. 5339-5348, (2000).

Feldstein, et al., "Coherence of thermal transitions in poly(N-vinyl pyrrolidone)-poly(ethylene glycol) compatible blends: 3. Impact of sorbed water upon phase behavior", Polymer, vol. 41, pp. 5439-5359, (2000).

Feldstein, et al., "Correlations between activation energy for debonding and that for self-diffusion in pressure-sensitive hydrogels", Proceed. 24th Annual Meeting Adhession Soc., pp. 137-140, (2001).

Feldstein, et al., "Contribution of molecular mobility to debonding of pressure-sensitive adhesive hydrogels", Polym. Mater. Sci. Eng., vol. 81, pp. 467-468, (1999).

Feldstein, et al., "Effect of hydrophilic matrix hydration on transdermal drug delivery kinetics: I. The matrix hydration In Vivo and In Vitro", Prediction of Percutaneous Penetration, vol. 4b, pp. 61-64, Brian, et al., (Eds.) (1996).

(56) References Cited

OTHER PUBLICATIONS

Feldstein, et al., "Effect of hydrophilic matrix hydration on transdermal drug delivery kinetics: II. In Vitro cytasine Delivery From Cypercuten TTS", Prediction of Percutaneous Penetration, vol. 4b, pp. 65-67, Brian, et al., (Eds.) (1996).
Feldstein, et al., "Effect of hydrophilic matrix hydration on transdermal drug delivery kinetics: III. In Vitro clonide delivery from clopercuten TTS", Prediction of Percutaneous Penetration, vol. 4b, pp. 68-70, Brian, et al., (Eds.) (1996).
Feldstein, et al., "Effect of hydrophilic matrix hydration on transdermal drug delivery kinetics: IV. In Vitro—In Vivo correlation," Prediction of Percutaneous Penetration, vol. 4b, pp. 71-73, Brian, et al., (eds.) (1996).
Feldstein, et al., "Effects of chains orientation, free volume and interaction on glass transition in poly(N-vinyl pyrrolidone)-poly(ethylene glycol) blends involving a stoichiometric hydrogen-Bbonded network complex", Polym. Mater. Sci. Eng., vol. 82, pp. 365-366, (2000).
Feldstein, et al., "General approach to the molecular design of hydrophilic pressure-sensitive adhesives," Proc. 25th Ann. Mtg. and 2nd World Congress on Adhesion and Related Phenomena, Orlando, FL, vol. 1, pp. 292-294 (2002).
Feldstein, et al., "Molecular insight into rheoligval and diffusion determinants of pressure sensitive adhesion", Proceed. 23rd Annual Meeting Adhesion Soc., pp. 54-56, (2000).
Feldstein, et al., "Peculiarities of glass transition temperature relation to the composition of poly(N-vinyl pyrolidone) blends with short chain poly(ethylene glycol)", Polymer, vol. 42, pp. 7719-7726, (2001).
Feldstein, et al., "Quantitative relationship between molecular structure and adhesion of PVP-PEG hydrogels", Polym. Mater. Sci Eng., vol. 81, pp. 465-466, (1999).
Feldstein, et al., "Relation of glass transition temperature to the hydrogen bonding degree and energy in poly(N-vinyl pyrrolidone) blends with hydroxyl-containing plasticizers: 2. Effects of poly(ethylene glycol) chain length", Polymer, vol. 42, pp. 981-990, (2001).
Feldstein, et al., "Universal hydrophilic drug-containing adhesive matrix for systemic and topical transdermal drug delivery", Proc. 1st World Meeting APGI/APV, Budapest, Sep. 2011, 2 pages, (1995).
Handbook of Pharmaceutical Excipients, Arther H. Kibbe, ed., 3rd ed., pp. 401-406, (2000).
Hawley's Condensed Chemical Dictionary, 14th Edition, Citation, "Oligomer, A polymer molecule of only a few monomer units (dimer, trimer, tetramer)", John Wiley and Sons, Inc., (2002).
International Search Report for PCT/US2000/18557 mailed Oct. 17, 2000.
International Search Report for PCT/US2001/21417 mailed Feb. 25, 2002.
International Search Report for PCT/US2002/13680 mailed Sep. 18, 2002.
International Search Report for PCT/US2002/14260 Mailed Sep. 17, 2002.
International Search Report for PCT/US2002/14725 mailed Sep. 27, 2002.
International Search Report for PCT/US2003/16408 Mailed Dec. 8, 2003.
International Search Report for PCT/US2003/039717 Mailed Jun. 28, 2004.
International Search Report for PCT/US2004/003443 Mailed Aug. 20, 2004.
International Search Report for PCT/US2004/011567 Mailed Jan. 10, 2006.
International Search Report for PCT/US2004/015448 Mailed Dec. 28, 2004.
International Search Report for PCT/US2004/029620 Mailed Jun. 1, 2005.
International Search Report for PCT/US2005/0002873 Mailed Apr. 27, 2005.
International Search Report for PCT/US2005/0034439 Mailed Jul. 19, 2006.
International Search Report for PCT/US2005/0046577 Mailed Jul. 26, 2006.
International Search Report for PCT/US/2005/028063 Mailed Apr. 28, 2006.
International Search Report for PCT/US/2005/032525 Mailed Mar. 17, 2006.
International Search Report for PCT/US/2006/000098 Mailed Nov. 3, 2006.
International Search Report for PCT/US2006/0003091 Mailed Oct. 11, 2006.
International Search Report for PCT/US2006/018500 Mailed Sep. 21, 2006.
Kotomin, et al., "Squeeze-recoil analysis of adhesive hydrogels and elastomers", Polym. Mater. Sci. Eng., vol. 81, pp. 425-426, (1999).
Kotomin, et al., "Durability and fracture of some visceolastic adhesives," Proceed. of the 23rd Annual Meeting of the Adhesion Soc., pp. 413-415, (2000).
MSDS (Material Safety Data Sheet), Lactic Acid, No. L0522, (2008).
Patent Abstracts of Japan, vol. 017, No. 055 (C-1023) Feb. 3, 1993 & JP 04 266818 A (Sekisui Chem Co Ltd), Sep. 22, 1992 abstract.
Roos, et al., "Probe tack investigation of poly(vinyl pyrrolidone)-poly(ethylene glycol) blends", Proceed. 24th Annual Meeting Adhesion Soc., pp. 277-279, (2001).
Sintov, et al., "Radiofrequency-driven skin microchanneling as a new way for electically assisted transdermal delivery of hydrophilic drugs", J. Contr.Release, vol. 89, pp. 311-320, (2003).
Supplementary European Search Report for EP04783729.9 Mailed Jun. 5, 2009.
Vartapian, et al., "Self-diffusion in poly(N-vinyl pyrrolidone)-poly-(ethylene glycol) systems", Colloid Polym. Sci., vol. 279, pp. 532-538, (2001).
Vartapian, et al., "Molecular dynamics in poly(N-vinyl pyrrolidone)-poly(ethylene glycol) blends by pulsed-field gradient NMR method: effects of aging, hydration and PEG chain length", Macromol. Chem. Phys., vol. 202, pp. 2648-2652, (2001).
International Search Report from related PCT Patent Application No. PCT/US2010/000081 mailed on Sep. 7, 2007, application published as WO 2010/083035 A3 on Jul. 22, 2010.
"Aquasorb® A-500 Cellulose Gum (CMC)", Hercules Incorporated, Aqualon Division, Product Data No. 4234, 2 pgs. (2005).
Barbucci et al. "Swelling behavior of carboxymethycelluiose hydrogels in relation to cross-linking, pH. and charge density", Macromolecules, vol. 33, No. 20, pp. 7475-7480 (2000).
EUDRAGIT® RL 100, "EUDRAGIT® RL 100 is a copolymer of ethyl acrylate, methyl methacrylate and a low content of methacrylic acid ester with quaternary ammonium groups. The ammonium groups are present as salts and make the polymers permeable", Product information, Accessed online from: http://eudragit.evonik.com/product/eudragit/en/products-services/eudragit-products/sustained-release-formulations/rl-100/pages/default.aspx. 1 page, accessed on Sep. 5, 2012.
EUDRAGIT® RS 100, "EUDRAGIT® RS 100 is a copolymer of ethyl acrylate, methyl methacrylate and a low content of methacrylic acid ester with quaternary ammonium groups. The ammonium groups are present as salts and make the polymers permeable", Product information, Accessed online from: http://eudragit.evonik.com/prodcut/eudragit/en/products-services/eudragit-products/sustained-release-formulations/rs-100/pages/default.aspx, 1 page, accessed on Sep. 5, 2012.
Evonic Industries, "EUDRAGIT® E 100: EUDRAGIT® E 100 is a cationic copolymer based on dimethylaminoethyl methacrylate, butyl methacrylate, and methyl methacrylate", Product information, Accessed Online form http://eudragit.evonik.com, 1 page, accessed on Apr. 21, 2011.
Evonic Industries, "EUDRAGIT® L 12.5 and EUDRAGIT® S 12,5", Product Information, Accessed Online from http://eudragit.evonik.com, 1 page (2011).

(56) References Cited

OTHER PUBLICATIONS

Evonic Industries, "EUDRAGIT® RL 12,5 and EUDRAGIT® RS 12,5", Product Information, Accessed Online from http://eduragit.evonick.com, 1 page (2011).

Evonic Industries, "EUDRAGIT® NE 30 D: EUDRAGIT® NE 30 D is the aquesous dispersion of a neutral copolymer based on ethyl acrylate and methyl methacrylate", Product Information, Accessed Online from http://eudragit.evonik.com, 1 page, Apr. 21, 2011.

Feldstein et al., "A new class of pressure-sensitive adhesives based on interpolymer and polymer-oligomer compleses". Polymer Science, vol. 51, No. 7, pp. 799-814 (2009).

Schehlmann "Polyvinylcaprolactam: physical and cosmetic properties of a new hair fixative resin", Lecture held at the IN-COSMETICS, SOFW-Journal-Sounderdruck, Dusseldorf, 6 pages (1997).

Whelan Polymer Technology Dictionary, Citation *Butyl Rubber*, Chapman Hall, 2-6 Boundry Row, London, UK, vol. 1, pp. 53 (1994).

\* cited by examiner

US 8,784,879 B2

TRANSDERMAL ADMINISTRATION OF TAMSULOSIN

CROSS-REFERENCE TO RELATED APPLICATIONS

This application claims priority to U.S. Provisional Patent Application No. 61/144,728, filed Jan. 14, 2009, which is incorporated by reference in its entirety.

TECHNICAL FIELD

This invention relates generally to the transdermal administration of tamsulosin and other active agents which are poorly soluble in the adhesive matrix.

BACKGROUND

Tamsulosin is a drug approved in the United States for the treatment of signs and symptoms of benign prostatic hyperplasia. It is marketed in an oral formulation under the trade name Flomax®. The R(−) stereoisomer is used for treatment. The approved oral doses are 0.4 mg/day and 0.8 mg/day. The chemical structure of tamsulosin is 5-[2-[[2-(2-ethoxyphenoxy)ethyl]amino]propyl]-2-methoxy-benzenesulfonamide:

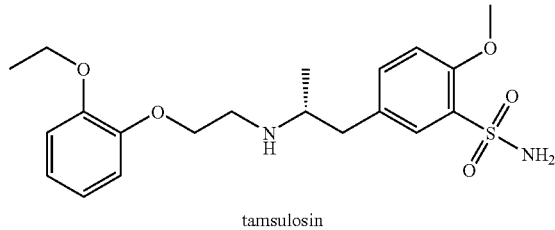 [SMILES: CCOc1ccccc1OCCN[C@H](C)Cc1ccc(OC)c(S(N)(=O)=O)c1]

tamsulosin

Tamsulosin is described in U.S. Pat. No. 5,447,958 to Niigata et al., assigned to Yamanouchi Pharmaceutical Co., Ltd. Therapeutically, it is believed to be an $\alpha_1$-adrenergic receptor antagonist acting preferentially on $\alpha_{1A}$ receptors. While it has therapeutic effects comparable to other $\alpha_1$ antagonists, its benzenesulfonamide structure makes it different chemically from other $\alpha_1$ antagonists in common clinical use (e.g., prazosin and terazosin).

In addition to treatment of signs and symptoms of benign prostatic hyperplasia, tamsulosin has been reported to be effective in the treatment of ureterolithiasis and has been studied as a treatment for painful ejaculation. The use of tamsulosin has also been considered or suggested for other urological conditions, for example evacuatory insufficiency in U.S. Pat. No. 6,861,070 and pathogenic vascular degradative modeling in the ilio-hypogastric-pudendal arterial bed in U.S. Pat. No. 6,787,553.

About twelve years before the present application, the transdermal administration of tamsulosin was taught in U.S. Pat. No. 5,843,472. Certain enhancer combinations are claimed there. It is believed that a permeation enhancer is needed for adequate transdermal administration of tamsulosin.

Despite the teachings of U.S. Pat. No. 5,843,472, there are no tamsulosin patches available in the United States. Transdermal delivery offers well-known advantages in avoiding sharp peak concentrations and side effects resulting from such concentrations. The pharmacokinetics of the oral Flomax formulation suffers from a considerable food effect, as documented in the package insert. Tamsulosin, like other $\alpha_1$ antagonists, has produced postural hypotension in some patients, which transdermal delivery may alleviate by avoiding high peak concentrations.

There is therefore a need for an improved transdermal patch which can deliver tamsulosin.

SUMMARY OF THE INVENTION

In an aspect of the invention, a composition for making a patch for the transdermal delivery of tamsulosin is provided. The composition comprises (a) at least about 1 wt % tamsulosin or a pharmaceutically acceptable salt of tamsulosin, (b) at least about 40 wt % polyisobutylene adhesive or hydrophobic synthetic rubber adhesive, (c) about 1-20 wt % of an aprotic solvent in which tamsulosin dissolves readily, (d) about 1-20 wt % of an unsaturated fatty acid or an alpha-hydroxy acid or a mixture of unsaturated fatty acids or alpha-hydroxy acids or of both unsaturated fatty acids and alpha-hydroxy acids, (e) a lipophilic permeation enhancer, and (f) a matrix modifier.

In a further aspect of the invention, a method of manufacturing a transdermal drug-in-adhesive patch for delivery of tamsulosin is provided. In the method, tamsulosin or a pharmaceutically acceptable salt of tamsulosin is dissolved in an aprotic solvent. The tamsulosin solution is combined with a lipophilic permeation enhancer and an unsaturated fatty acid. A matrix modifier is added and the resulting solution is homogenized. The solution is then mixed with a polyisobutylene adhesive or hydrophobic synthetic rubber adhesive in a suitable solvent. It may be solvent cast or extruded.

DETAILED DESCRIPTION OF THE INVENTION

Figure 1:
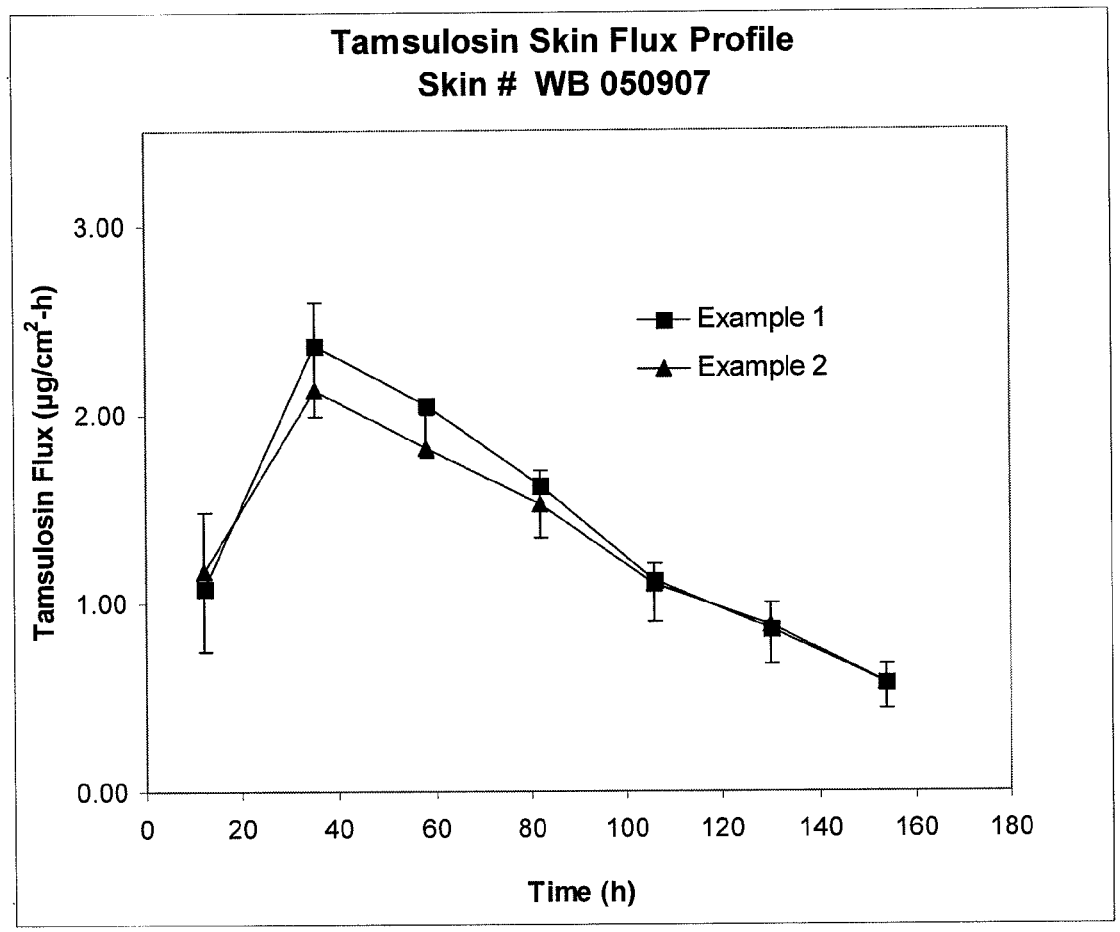
FIG. 1 depicts the results of a skin permeation test for Examples 1 and 2.

It is to be understood that, unless otherwise indicated, this invention is not limited to specific polymers, oligomers, crosslinking agents, additives, manufacturing processes, or adhesive products. It is also to be understood that the terminology used herein is for the purpose of describing particular embodiments only, and is not intended to be limiting.

In describing and claiming the present invention, the following terminology will be used in accordance with the definitions set out below.

The singular forms "a," "an," and "the" include plural referents unless the context clearly dictates otherwise. Thus, for example, reference to "a hydrophilic polymer" includes not only a single hydrophilic polymer but also two or more hydrophilic polymers that may or may not be combined in a single composition, reference to "a plasticizer" includes a single plasticizer as well as two or more plasticizers that may or may not be combined in a single composition, and the like.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also disclosed, as well as the range of values greater than or equal to 1 µm and the range of values less than or equal to 8 µm.

When we refer to an adhesive matrix in this application, we include matrices which are made in one piece, for example via solvent casting or extrusion. We also include, however, matrices which are made in two or more portions which are then pressed or joined together.

A. Patches and Compositions for Making them

In an aspect of the invention, a composition for making a patch for the transdermal delivery of tamsulosin is provided. The composition comprises (a) tamsulosin or a pharmaceutically acceptable salt of tamsulosin, (b) polyisobutylene adhesive, (c) an aprotic solvent in which tamsulosin dissolves readily, (d) an unsaturated fatty acid, (e) a lipophilic permeation enhancer, and (f) a matrix modifier.

Among the obstacles standing in the way of a good tamsulosin transdermal patch are (a) the poor solubility of tamsulosin in conventional transdermal reservoir materials such as polyisobutylene (PIB) adhesives and (b) the skin irritation which may result from the active itself or from the additives e.g. permeation enhancers. For many drug substances the free base form is readily soluble in transdermal adhesives, whereas oral formulations tend to use salt forms of the drug substance. For tamsulosin, however, both aqueous and organic solvent solubility are generally poor.

Transdermal administration of tamsulosin with conventional transdermal adhesives requires some way of overcoming the solubility problem. A potential solution is the use of one of the relatively few solvents in which tamsulosin is readily soluble, and using additional excipients to allow the tamsulosin solution to be mixed with the polyisobutylene adhesive and to produce a pharmaceutically acceptable dosage form (e.g., from the irritation point of view).

For example, dimethylsulfoxide (DMSO) may potentially be used. The table below gives some data on the solubility of tamsulosin in DMSO and in mixtures of DMSO and water:

| Water in DMSO (w/w %) | Solubility of Tamsulosin (w/w %) | Solubility of Tamsulosin (mg/g) | Solubility of Tamsulosin (Log Cs) |
| --- | --- | --- | --- |
| 0 | 23.0 | 230 | 2.362 |
| 8.85 | 7.29 | 72.9 | 1.863 |
| 16.85 | 3.02 | 30.2 | 1.479 |
| 29.19 | 0.52 | 0.52 | 0.715 |

It may be seen from the data in the table above that as long as the water content of the DMSO is maintained below certain limits, the tamsulosin may be solubilized in DMSO-water blends.

A patch may also be made with certain other aprotic solvents, for example dimethylacetamide (DMAc) and N-methylpyrrolidone (NMP), rather than DMSO.

It is also necessary to maintain skin irritation at no more than a tolerable level. Conventionally, the use of DMSO is seen as potentially increasing skin irritation. For example, U.S. Pat. No. 4,855,294 suggests that patches containing dimethyl sulfoxide (DMSO) would require an emollient, for example glycerin, to be sufficiently non-irritating.

It has surprisingly been discovered that appropriate proportions of DMSO, a co-solubilizer, and a lipophilic permeation enhancer allow tamsulosin to be delivered with acceptable irritation and good transdermal flux from a polyisobutylene adhesive.

The co-solubilizer may be, for example, an unsaturated fatty acid or α-hydroxy acid. The co-solubilizer may be, for example, $CH_3(CH_2)_m(CH=CH)_nCOOH$ where m is an integer between 8 to 16, n is from 1 to 3, and the n CH=CH units may be arranged in any order within the chain of m $CH_2$. Alternatively, the co-solubilizer may be R(OHCHCOOH) where R is an alkyl group with 1 to 6 carbons arranged either linear or branched, in an enantiomeric or racemic form. The co-solubilizer may be, for example, oleic acid, linoleic acid, or linolenic acid (fatty acids). The co-solubilizer may be, for example, lactic acid or glycolic acid (α-hydroxy acids).

The lipophilic permeation enhancer may be chosen from a wide range of such compounds known in the art. A review of permeation enhancers is found, for example, in Nadir Büyüktimkin et al., "Chemical Means of Transdermal Drug Permeation Enhancement," chapter 11 of *Transdermal and Topical Drug Delivery Systems* (Tapash K. Ghosh et al. eds. 1997).

A useful class of lipophilic permeation enhancers has the formula $CH_3(CH_2)_mCOOR'$. Here m is an integer in the range of 6 to 14, and R' is a C1-C3 lower alkyl residue that is either unsubstituted or substituted with one, two, or three hydroxyl groups. A further useful class of lipophilic permeation enhancers has the formula $CH_3(CH_2)_m—OCOCHR_1R_2$, where m is as above and R1 and R2 are hydrogen, hydroxyl, or C1-C2 lower alkyl, and at least one of R1 and R2 is hydroxyl or both R1 and R2 are hydrogen. Preferred permeation enhancers for use with the patches of the invention include methyl laurate, propylene glycol monolaurate, glycerol monolaurate, glycerol monooleate, lauryl lactate, myristyl lactate, and dodecyl acetate.

A matrix modifier is also useful in making a transdermal patch comprising tamsulosin. Without wishing to be bound by theory, it is believed that the matrix modifier facilitates homogenization of the adhesive matrix. Sorption of hydrophilic moieties is a possible mechanism for this process. Thus, known matrix modifiers which are to some degree water-sorbent may be used. For example, possible matrix modifiers include colloidal silicone dioxide, fumed silica, cross-linked polyvinylpyrrolidone (PVP), soluble PVP, cellulose derivatives (e.g. hydroxypropyl cellulose (HPC), hydroxyethylcellulose (HEC)), polyacrylamide, polyacrylic acid, a polyacrylic acid salt, or a clay such as kaolin or bentonite. An exemplary commercial fumed silica product is Cab-O-Sil (Cabot Corporation, Boston, Mass.). The hydrophilic mixtures described in U.S. Published Patent Application No. 2003/0170308 may also be employed, for example mixtures of PVP and PEG or of PVP, PEG, and a water-swellable polymer such as Eudragit L100-55.

Patches of the invention may be designed to be replaced, for example, once per week, so that they continue delivering significant amounts of active at 168 hours from patch application. With some patches of the invention, the time of maximum tamsulosin flux may be at least 60 hours, at least 75 hours, or at least 90 hours.

In understanding the performance of patches of the invention, it may be useful to consider the comparative flux of tamsulosin and DMSO. In general DMSO is present in larger amounts in the patch, for example in a DMSO/tamsulosin weight ratio of at least about 1.2, at least about 1.4, or at least about 1.8. The DMSO will generally be released more rapidly from the patch than the tamsulosin, as seen in Example 12 below. It is desirable, however, to control the ratio of tamsulosin/DMSO cumulative release. For example, the ratio of tamsulosin/DMSO cumulative release may be at least about 0.05 in the time period 72 hours to 120 hours after administration or at least about 0.08, 0.1, or 0.15 in the time period 120 hours to 168 hours. The ratio may also be, for example, no more than about 0.15 in the first 72 hours, no more than about 0.38 in the time period 72 hours to 120 hours, and no more than about 0.5, 0.6, or 0.8 in the time period from 120 to 168 hours.

As noted above, an alpha-hydroxy acid may be employed in the patches. The molar ratio of this acid to tamsulosin may be, for example, at least about 0.05, at least about 0.10, or at least about 0.20.

B. Methods of Making Patches

In a further aspect of this invention, a transdermal patch comprising tamsulosin is made by a process in which the active is used in the form of tamsulosin hydrochloride. For a variety of reasons, tamsulosin hydrochloride is an advantageous starting form of the active. For example, in the commercial oral dosage form, tamsulosin is in the hydrochloride form.

The following describes generally a class of processes for manufacturing a transdermal drug-in-adhesive patch for delivery of tamsulosin. Tamsulosin or a pharmaceutically acceptable salt of tamsulosin is dissolved in an aprotic solvent. The tamsulosin solution is combined with a lipophilic permeation enhancer, an optional organic solvent, and an unsaturated fatty acid. A matrix modifier is added and the resulting solution is homogenized. The solution is then mixed with a polyisobutylene adhesive or hydrophobic synthetic rubber adhesive in a suitable solvent. It may be, for example, solvent cast or extruded.

Example 1 describes a method for making a transdermal tamsulosin patch using tamsulosin base. As may be seen, a peak in vitro flux of above about 2 $\mu g/cm^2$-h is achieved.

In order to produce a transdermal patch which is made with tamsulosin salts e.g., tamsulosin hydrochloride, it is helpful to use a neutralizing agent as a process aid and mix it into the solution containing the tamsulosin salt prior to mixing that solution with the polyisobutylene adhesive, allowing a period of reaction in that solution. The neutralizing agents should have pKa equivalent or higher than that of tamsulosin. These neutralizing agents are alkali hydroxides and alkali salts (e.g. NaOH, KOH, $Na_2CO_3$, etc). Examples 2, 3, and 7 show some ways in which patches can be made with tamsulosin hydrochloride. With a suitable neutralizing agent, the final patch contains sufficient tamsulosin base to provide adequate delivery of the active across skin, as shown by the results of the examples. For example, a peak flux of at least about 0.01 $\mu g/cm^2$-hr, at least about 1.0 $\mu g/cm^2$-hr, at least about 1.5 $\mu g/cm^2$-hr, or at least about 2.0 $\mu g/cm^2$-hr may be achieved. (Similar fluxes can be achieved with patches made starting with tamsulosin base.)

It is in general desirable to have a relatively low coat weight in a transdermal formulation. One reason for this is that with lower coat weights and thus thinner patches, it may be possible to solvent-cast the patch rather than extruding it, a process which is somewhat more complex. For example, it may be desirable to have a coat weight of no more than about 10 $mg/cm^2$, about 15 $mg/cm^2$, about 20 $mg/cm^2$, about 25 $mg/cm^2$, about 30 $mg/cm^2$, about 35 $mg/cm^2$, about 40 $mg/cm^2$, or about 50 $mg/cm^2$. With poorly soluble drugs a limitation on the coat weight is the need to have sufficient adhesive matrix per $cm^2$ of skin surface to hold the needed amount of drug to achieve extended duration of delivery with a patch of reasonable size. Thus the use of particular solvents as disclosed in this application can be helpful in achieving a desirably low coat weight, by allowing a higher weight ratio of active to total adhesive matrix. For example, it may be desirable to have a ratio of at least about 1% active to total adhesive matrix, at least about 2% active to total adhesive matrix, at least about 3%, at least about 3.5%, at least about 4%, or at least about 5%.

As noted earlier, the patches of the invention may be made, for example, by melt extrusion or by solvent casting. In an extrusion process, the components of the composition are weighed out and then admixed, for example using a Brabender or Baker Perkins Blender, generally although not necessarily at an elevated temperature, e.g., about 90 to 170° C., typically 100 to 140° C. Solvents may be added if desired. The resulting composition can be extruded using a single or twin extruder, or pelletized. Alternatively, the individual components can be dissolved or melted one at a time, and then mixed prior to extrusion. The composition can be extruded to a desired thickness directly onto a suitable substrate or backing member. The composition can be also extruded first, and then be pressed against a backing member or laminated to a backing member.

Alternatively, the compositions may be prepared by solution casting, by admixing the components in a suitable solvent, at a solids concentration which may be in the range of about 15 to 60% w/v. The solution is cast onto a substrate, backing member or releasable liner, as above. Both admixture and casting are preferably carried out at ambient temperature. The material coated with the film is then baked at a temperature above ambient, for example a temperature in the range of about 40 to 130° C., for a time period in the range of 5 minutes to 70 minutes.

C. Other Possible Components in Patches

The patches of the invention may comprise one or more additional actives to be administered with the tamsulosin. Corticosteroids have been suggested, for example, as useful for lithiasis in conjunction with tamsulosin. The patent literature suggests a large number of cotherapy combinations with tamsulosin. Exemplary recent U.S. patents mentioning concurrent administration of tamsulosin and other actives include U.S. Pat. Nos. 7,354,581, 7,332,482, 7,317,029, 7,288,558, 7,271,175, 7,211,599, 7,138,405, and 6,423,719.

In addition, the compositions and methods of the invention should be useful for making patches containing other actives which have adhesive matrix solubility issues similar to tamsulosin, so that they are dissolvable in a desired adhesive matrix no more than about 0.5%, 1% or 2%. Thus, these compositions and methods, although developed for tamsulosin, may be useful for the delivery of actives other than tamsulosin, not in combination with tamsulosin.

Various additives, known to those skilled in the art, may be included in transdermal compositions. Optional additives include opacifiers, antioxidants, fragrance, colorant, gelling agents, thickening agents, stabilizers, and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

While it is believed that the low irritation shown to be achieved in Examples 4-6 is acceptable, the formulation may also contain irritation-mitigating additives to minimize or eliminate the possibility of skin irritation or skin damage resulting from the drug, the enhancer, or other components of the formulation. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. Corticosteriods are also known in art as irritation-mitigating additives.

It is possible to employ a combination of permeation enhancers. The permeation enhancers listed in Büyüktimkin et al., supra, provide a range of choices to the formulator. Possible enhancers include, for example, the following: ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate ("PEGML"; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid.

In a common overall design of a transdermal patch, there is provided an adhesive matrix containing active as described above. The adhesive matrix may contain additional components besides those already described, for example a nonwoven material which may, for example, assist in providing mechanical stability. The adhesive matrix may be provided in the form of a thin square or circle or other usually convex shape of flat material. On one side of the flat adhesive matrix, there is a release liner, and on the other side a backing layer. The release liner is intended to be removed before use, and the backing layer is intended to remain attached to the adhesive matrix in use. It may be convenient to have multiple adhesive layers, not all necessarily containing active.

The backing layer of the transdermal drug delivery device functions as the primary structural element of the transdermal system and provides the device with flexibility, drape and, optionally, occlusivity. The material used for the backing layer should be inert and incapable of absorbing drug, enhancer or other components of the pharmaceutical composition contained within the device. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 1 micron to about 250 microns in thickness, and may, if desired, be pigmented, metallized, or provided with a matte finish suitable for writing. The layer is preferably occlusive, i.e., is preferably impermeable to moisture, for example with an MVTR (moisture vapor transmission rate) less than about 50 g/m²-day.

The release liner is desirably made from a drug/vehicle impermeable material, and is a disposable element which serves only to protect the device prior to application. Typically, the release liner is formed from a material impermeable to the components of the device and the pharmaceutical composition contained therein.

Additional layers, e.g., intermediate fabric or nonwoven layers and/or rate-controlling membranes, may also be present in transdermal patches of the invention. Fabric or nonwoven layers may be used to improve mechanical stability, while a rate-controlling membrane may be used to control the rate at which a component permeates out of the device.

The practice of the present invention will employ, unless otherwise indicated, conventional techniques of drug formulation, particularly topical drug formulation, which are within the skill of the art. Such techniques are fully explained in the literature. See, e.g., *Remington: The Science and Practice of Pharmacy* (19th ed., Easton, Pa.: Mack Publishing Co., 1995).

It is to be understood that while the invention has been described in conjunction with preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

EXAMPLES

The following examples are put forth so as to provide those of ordinary skill in the art with a complete disclosure and description of how to manufacture the transdermal patches of the invention, and are not intended to limit the scope of that which the inventors regard as the invention. Efforts have been made to ensure accuracy with respect to numbers (e.g., amounts, temperatures, etc.) but some errors and deviations should be accounted for. Unless indicated otherwise, parts are parts by weight, temperature is in degrees Celsius (° C.), and pressure is at or near atmospheric.

Example 1

Tamsulosin base was accurately weighed and dissolved in an aprotic solvent, dimethylsulfoxide, by vortexing. Lauryl lactate and oleic acid were added and mixed into the DMSO/drug solution. The heterogeneous mixture was homogenized with Cab-O-Sil. The homogenate was mixed with polyisobutylene/n-heptane solution for more than 3 hr to form a uniform coating mix. The formulation was coated and dried. The final formulation has a composition as given in the following table.

| | |
|---|---|
| PIB | 69.50% |
| Cab-O-Sil | 7.00% |
| Tamuslosin | 3.50% |
| Lauryl lactate | 6.00% |

| | |
|---|---|
| Oleic acid | 5.00% |
| DMSO | 9.00% |
| Total | 100.0% |

The PIB adhesive solution was prepared by mixing Oppanol B-100, Oppanol B-12, and Indopol H1900 in heptane.

The formulations were tested for tamsulosin skin penetration using cadaver skin on Franz diffusion cells. An in vitro skin flux study was done at 32-35° C. using phosphate buffer pH 6.0 with 0.01% sodium azide as receptor media. Samples at different time intervals were collected and tamsulosin was quantified by reversed phase HPLC method. Results are given in FIG. 1.

Example 2

Tamsulosin HCl is accurately weighed and dissolved in an aprotic solvent, dimethylsulfoxide, by vortexing. An appropriate volume of 2N aqueous sodium hydroxide is mixed with the tamsulosin-HCl salt solution and stirred at ambient temperature for 22 hours.

Following completion of the reaction as described above, lauryl lactate and oleic acid were added. The mixture was homogenized with Cab-O-Sil. The homogenate was mixed with polyisobutylene/n-heptane solution for more than 3 hr to form a uniform coating mix. The formulation was coated and dried. The final formulation has a composition as given in the following table

| | |
|---|---|
| PIB | 68.86% |
| Cab-O-Sil | 7.00% |
| Tamuslosin-HCl | 3.80% |
| Lauryl lactate | 6.00% |
| Oleic acid | 5.00% |
| NaOH | 0.34% |
| DMSO | 9.00% |
| Total | 100.0% |

The formulation was tested for skin penetration as in Example 1. Results are given in FIG. 1.

Example 3

Figure 2:
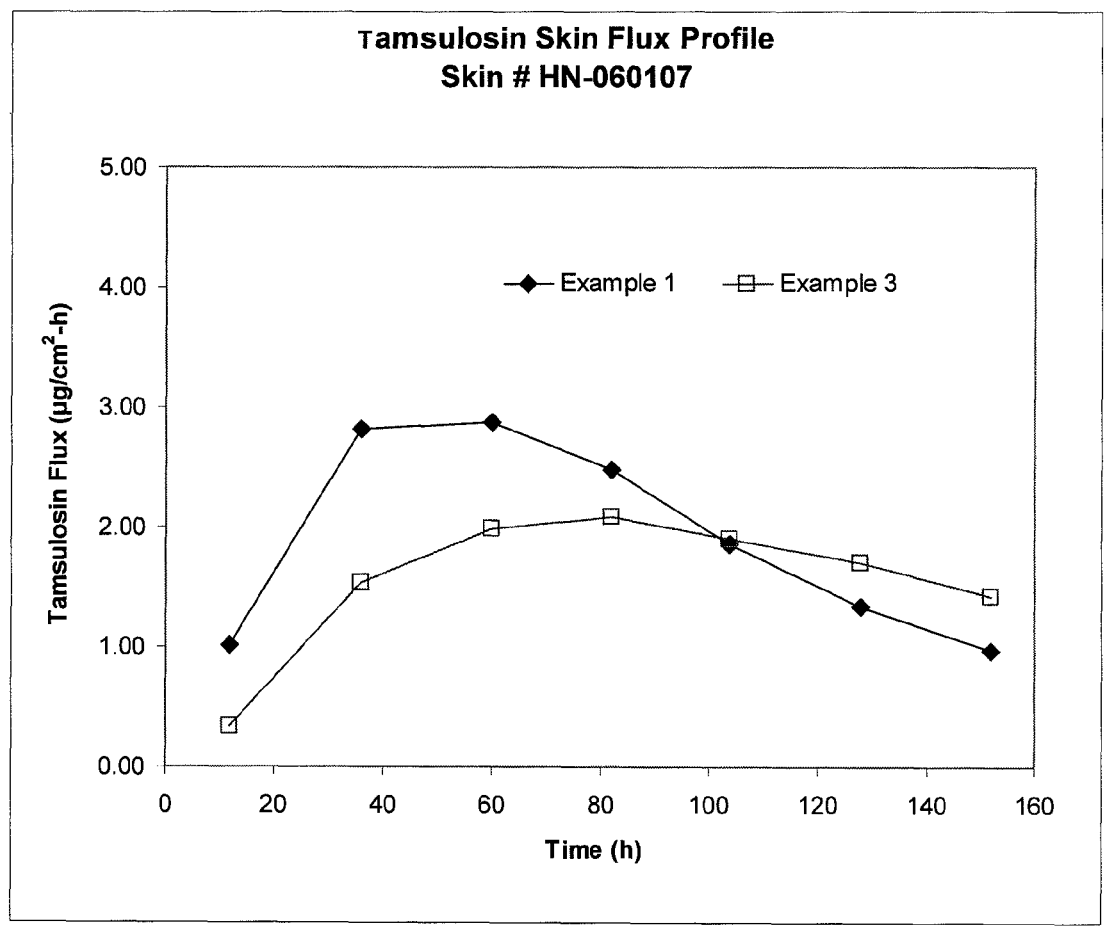
FIG. 2 depicts the results of a skin permeation test for Examples 1 and 3.

Same as Example 2, except 20% methanolic sodium hydroxide solution was used in place of aqueous sodium hydroxide. The reaction mixture remained clear after reaction. The formulation was tested for skin penetration as in Example 1. Results are given in FIG. 2. The Example 1 formulation was tested again for skin flux using different skin. Results are given in FIG. 2.

Examples 4-6

Formulation and Irritation Testing

Examples 4, 5, and 6 formulations were prepared from tamsulosin base using the ingredient combinations in the following table:

| Ingredient | Ex 4 | Ex 5 | Ex 6 |
|---|---|---|---|
| PIB adhesive | 75.5 | 69.5 | 74.5 |
| DMSO | 3.0 | 9.0 | 6.0 |
| Lauryl lactate | 6.0 | 6.0 | 6.0 |
| Oleic acid | 5.0 | 5.0 | 3.0 |
| Cab-O-Sil | 7.0 | 7.0 | 7.0 |
| Tamsulosin base | 3.5 | 3.5 | 3.5 |

Tamsulosin base was dissolved in DMSO. Lauryl lactate and oleic acid were added to the DMSO drug solution. Cab-O-Sil was suspended in the solution by homogenization and then the solution was mixed with PIB solution. The adhesive formulation solution was coated at 3 mils on drying. The two adhesive layers were laminated on each side of a Reemay 2250 non-woven polyester fabric layer. The PIB adhesive was prepared by mixing Oppanol B-100, Oppanol B-12, and Indopol H1900 in heptane.

A skin irritation study was done on New Zealand white rabbits. The test articles (active formulation) and control (placebo formulation) were applied to the skin of same animal for 24 hr. A primary irritation index (PII) was calculated based on erythema and edema scores at 24 and 72 hr after patch removal. The results are given in the following table. The active and placebo formulations of Examples 4, 5 and 6 were classified as mildly skin irritating as the primary skin irritation index for all test articles was in the range of 0.9 to 1.9.

Example 7

Formulation, In Vitro Skin Flux, and Irritation Testing

A scale up batch of Tamsulosin HCl adhesive mix was prepared based on the composition as given in the following table.

| Material Name | Wet Formula % | Dry Formula % |
|---|---|---|
| PIB adhesive mix | 40.165 | 69.2 |
| Dimethylsulfoxide | 12.250 | 9.0 |
| Tamsulosin HCl | 1.330 | 3.8 |
| NaOH, added as 2N aqueous solution | 1.610 | — |
| Lauryl Lactate | 2.450 | 6.0 |
| Organic solvent mix | 37.96 | — |
| Oleic Acid | 1.750 | 5.0 |
| Cab-O-Sil | 2.450 | 7.0 |
| Total | 100.000 | 100.0 |

Figure 3:
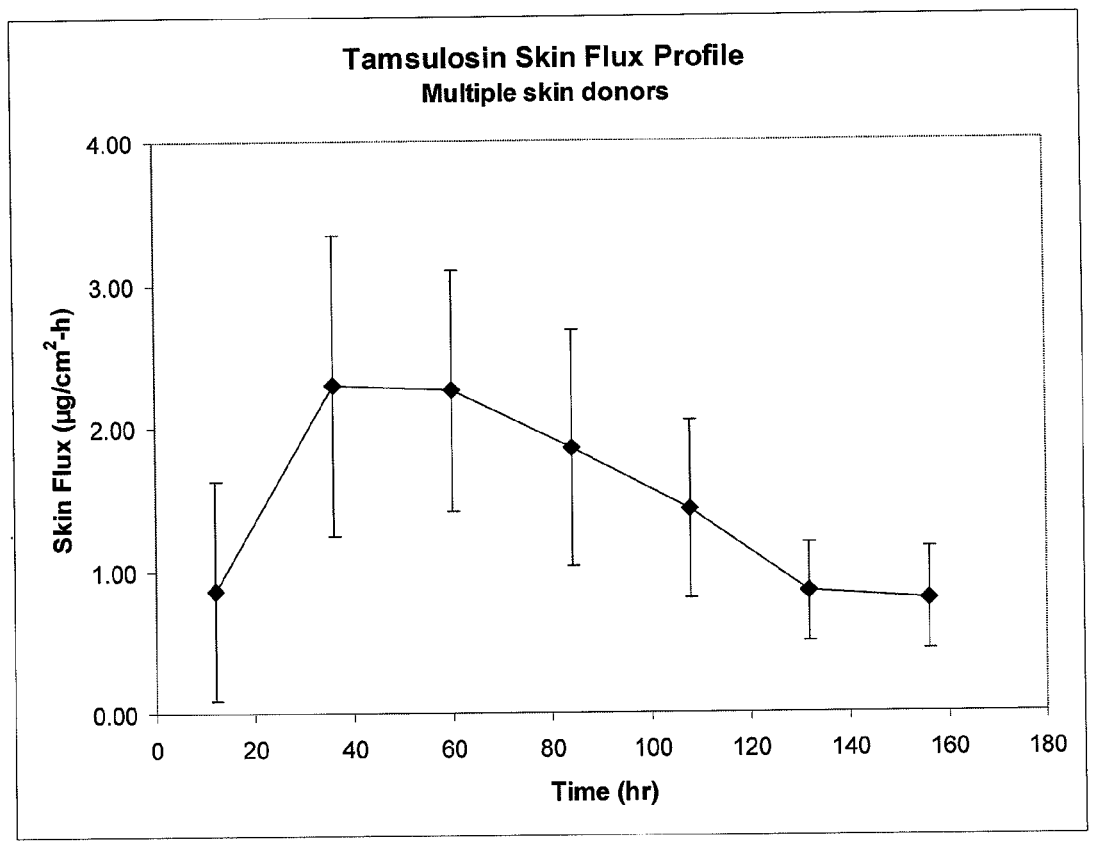
FIG. 3 depicts the results of a skin permeation test for Example 7.

Tamsulosin HCl transdermal delivery system (Tamsulosin HCl TDS) was prepared from the mix and irritation was tested. Tamsulosin HCl was dissolved in dimethylsulfoxide in a glass bottle. 2N NaOH solution in water was mixed with the tamsulosin-HCl salt solution and stirred. Following completion of the reaction described above, the solution was transferred to a dispersion mixer. Then lauryl lactate and oleic acid was added with the organic solvents and the mixture was dispersed with Cab-O-Sil. The dispersion homogenate was mixed with polyisobutylene/n-heptane solution in a mixing tank until a uniform coating mix is formed. The formulation was coated and dried. The formulation was tested for skin penetration as in Example 1 with multiple donors. Results are given in FIG. 3.

A skin irritation study was done on Specific Pathogen Free New Zealand white rabbits. Test articles (active formulation) and controls (placebo formulation) were applied on intact skin of the same animal for 24 hr. A primary irritation score (PIS) or index (PII) were calculated based on erythema and edema scores at 24, 48 and 72 hr after patch removal. Both test and placebo test articles were classified as slightly irritating, having primary irritation score or index in the range of 0.9 to 1.9.

Example 8

Figure 4:
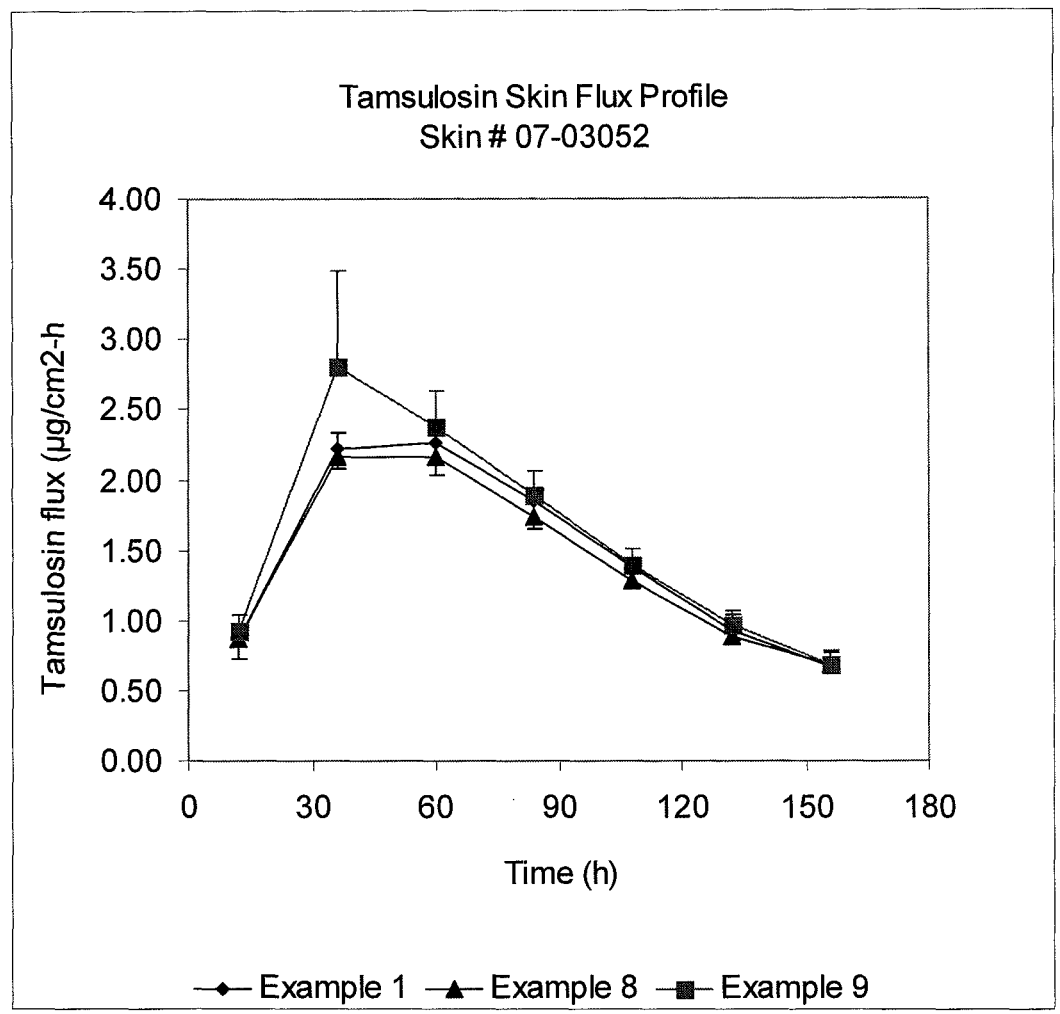
FIG. 4 depicts the results of a skin permeation test for Examples 8 and 9, with an Example 1 patch used as a reference.

Same as Example 1, except that 5.0% linoleic acid was used instead of oleic acid. The formulation was tested for skin penetration as in Example 1. Results are given in FIG. 4.

Example 9

Same as Example 1, except that 5.0% linolenic acid was used instead of 5.0% oleic acid. The formulation was tested for skin penetration as in Example 1. Results are given in FIG. 4.

Example 10

Figure 5:
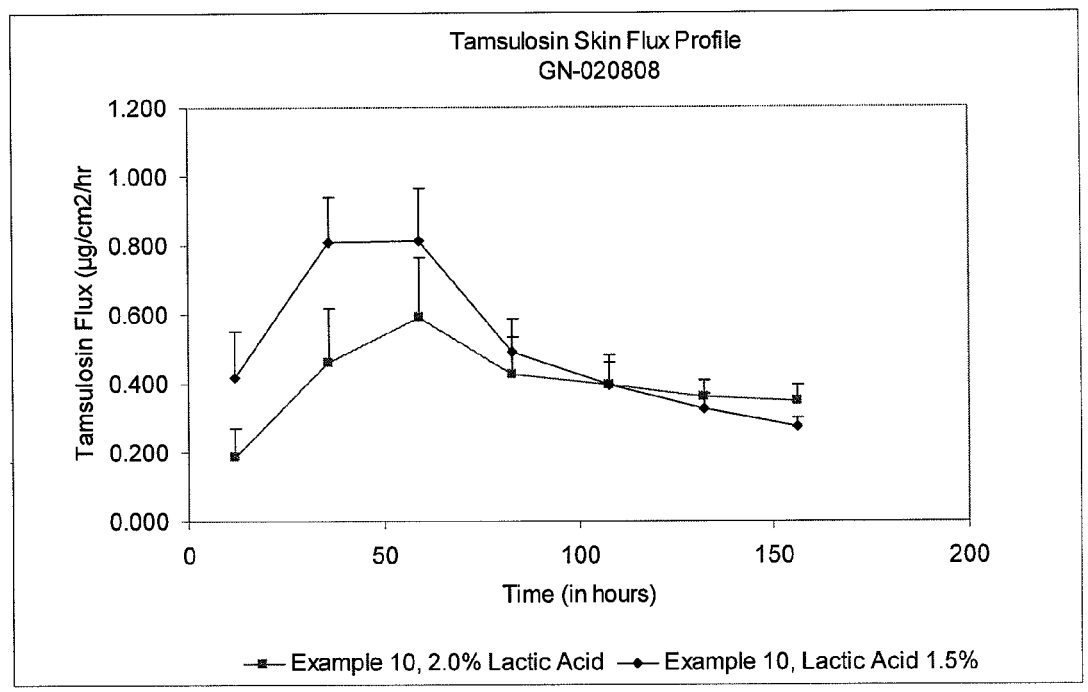
FIG. 5 depicts the results of a skin permeation test for Example 10.

Same as Example 1, 2.0 and 1.5% of lactic acid (an α-hydroxy acid) were used instead of oleic acid. The formulation was tested for skin penetration as in Example 1. Results are given in FIG. 5.

Example 11

Four formulations C1, C2, C3, C4 were prepared as described above with the following compositions.

|  | C1 (wt %) | C2 (wt %) | C3 (wt %) | C4 (wt %) |
| --- | --- | --- | --- | --- |
| Tamsulosin base | 7.0 | 7.0 | 9.0 | 9.0 |
| Colloidal silica | 7.0 | 7.0 | 7.0 | 7.0 |
| Oleic acid | 5.0 | 5.0 | 5.0 | 5.0 |
| Lactic acid | 2.0 | 2.0 | 2.75 | 2.75 |
| Dimethysulfoxide | 10.0 | 10.0 | 10.0 | 10.0 |
| Lauryl lactate | 6.00 | 6.00 | 6.00 | 6.00 |
| PIB adhesive mix | 63.0 | 63.0 | 60.25 | 60.25 |
| Dry thickness | 6.0 mils | 12.0 mils | 6.0 mils | 12.0 mils |

To achieve the 12 mil thickness, a quadruple casting process was used.

Figure 6A:
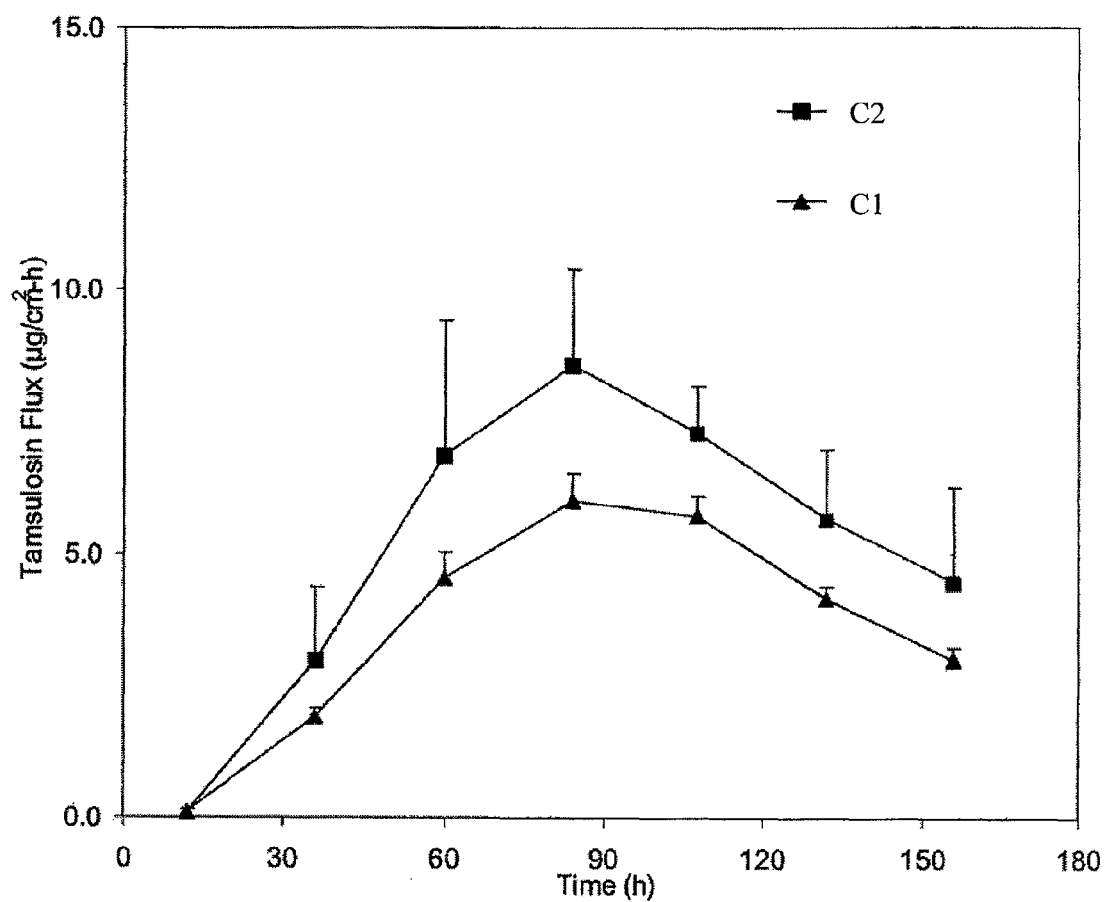
FIGS. 6A-6B depicts the results of a skin permeation test for Example 11.
Figure 6B:
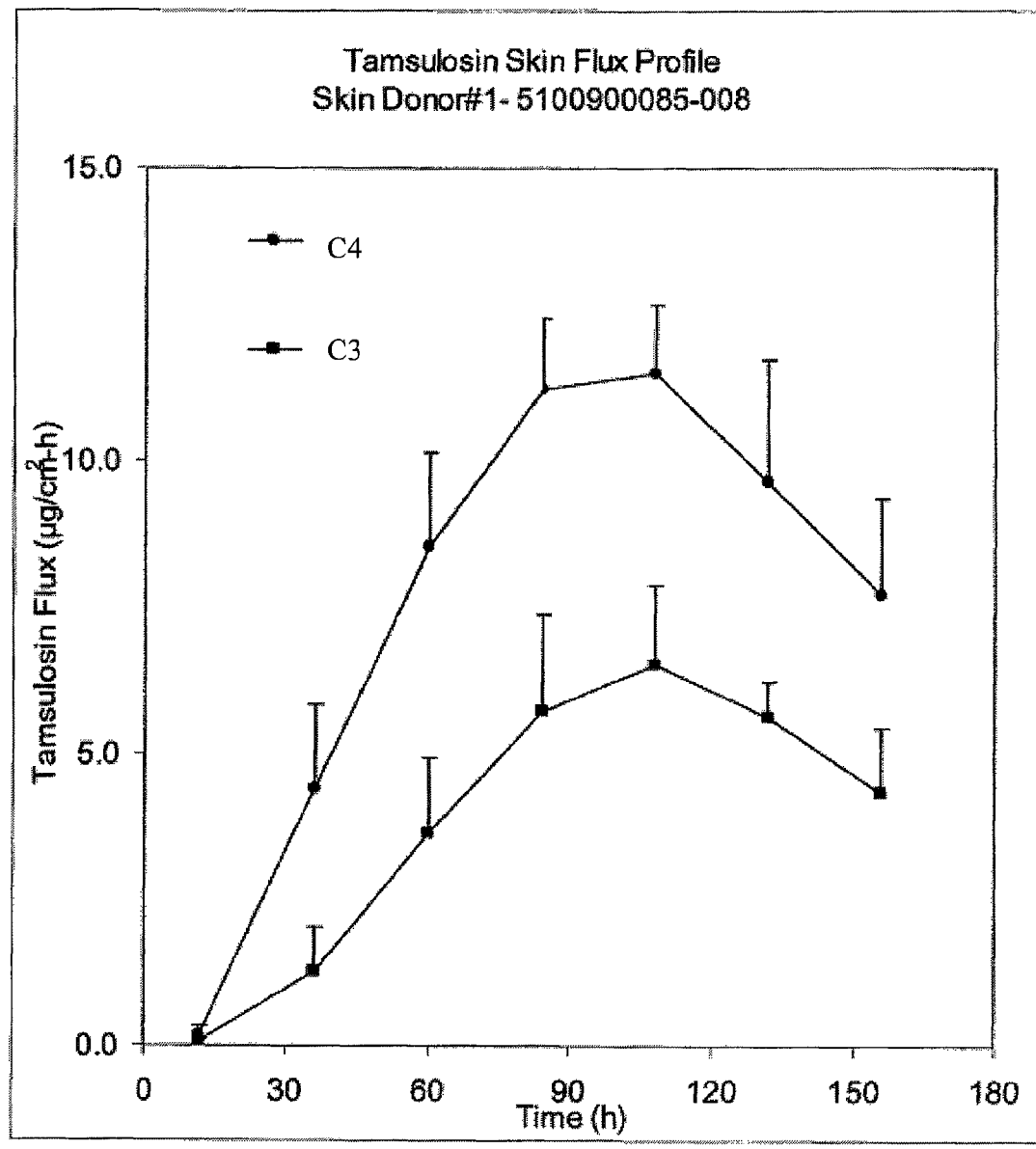

FIGS. 6A and 6B depict the tamsulosin release achieved with formulations C1 through C4. As may be seen, the thicker formulations achieve higher fluxes. The testing was done with cadaver skin described as high permeability.

Example 12

Further patches C5, C6, and C7 were prepared as shown in the following table

|  | C5 (wt %) | C6 (wt %) | C7 (wt %) |
| --- | --- | --- | --- |
| Tamsulosin base | 9.0 | 9.0 | 9.0 |
| Colloidal silica | 7.0 | 7.0 | 7.0 |
| Oleic acid | 5.0 | 5.0 | 5.0 |
| Lactic acid | 3.0 | 3.0 | 3.0 |
| Dimethylsulfoxide | 10.0 | 10.0 | 10.0 |
| Lauryl lactate | 6.00 | 6.00 | 6.00 |
| PIB adhesive mix | 60.0 | 60.0 | 60.0 |
| Dry thickness | 6.0 mils | 10.0 mils | 12.0 mils |

For patches C5, C6, and C7, both tamsulosin and DMSO release were measured in a Franz diffusion cell. The patches were tested against four lots of cadaver skin.

The following table gives the cumulative release of tamsulosin and DMSO in micrograms/cm$^2$, and the ratio of tamsulosin to DMSO cumulative release, for patches C5, C6, and C7:

| Time (h) | DMSO C5 | Tamsulosin C5 | DMSO C6 | Tamsulosin C6 | Ratio C5 | Ratio C6 |
| --- | --- | --- | --- | --- | --- | --- |
| 24 | 533.62 | 6.79 | 929.25 | 11.47 | 0.01 | 0.01 |
| 48 | 1090.88 | 70.31 | 1651.05 | 76.78 | 0.06 | 0.05 |
| 72 | 1399.20 | 199.49 | 2011.94 | 195.03 | 0.14 | 0.10 |
| 96 | 1544.37 | 346.86 | 2163.58 | 329.54 | 0.22 | 0.15 |
| 120 | 1609.56 | 491.05 | 2229.31 | 466.23 | 0.31 | 0.21 |
| 144 | 1638.04 | 615.19 | 2257.65 | 591.09 | 0.38 | 0.26 |
| 168 | 1649.40 | 729.69 | 2270.15 | 706.37 | 0.44 | 0.31 |

| Time (h) | DMSO C7 | Tamsulosin C7 | Ratio C7 |
| --- | --- | --- | --- |
| 24 | 786.12 | 6.02 | 0.01 |
| 48 | 1892.56 | 68.76 | 0.04 |
| 72 | 2607.60 | 230.81 | 0.09 |
| 96 | 2925.31 | 439.46 | 0.15 |
| 120 | 3097.52 | 667.79 | 0.22 |
| 144 | 3175.08 | 881.95 | 0.28 |
| 168 | 3214.69 | 1089.49 | 0.34 |

We claim:

1. A composition for making a patch for the transdermal delivery of tamsulosin, the composition comprising (a) at least 1 wt % tamsulosin or a pharmaceutically acceptable salt of tamsulosin, (b) at least 40 wt % polyisobutylene adhesive or hydrophobic synthetic rubber adhesive, (c) about 1-20 wt % of an aprotic solvent in which tamsulosin dissolves, (d) about 1-20 wt % of an unsaturated fatty acid or an alpha-hydroxy acid or a mixture of unsaturated fatty acids or alpha-hydroxy acids or of both unsaturated fatty acids and alpha-hydroxy acids, (e) a lipophilic permeation enhancer, and (f) a matrix modifier.

2. The composition of claim 1, wherein at least a portion of the tamsulosin is present in the form of tamsulosin HCl.

3. The composition of claim 2, further comprising a neutralizing agent.

4. The composition of claim 3, wherein the neutralizing agent has a pKa equivalent to or higher than that of tamsulosin.

5. The composition of claim 3, wherein the neutralizing agent comprises an alkali hydroxide, an alkali salt, or an amine.

6. The composition of claim 5, wherein the neutralizing agent comprises sodium hydroxide or potassium hydroxide.

7. The composition of claim 5, wherein the neutralizing agent comprises an alkali salt selected from the group consisting of sodium carbonate, potassium carbonate, sodium silicate, and potassium silicate.

8. The composition of claim 4, wherein the neutralizing agent comprises substituted or non-substituted alkyl amines.

9. The composition of claim 8, wherein the neutralizing agent comprises ethanolamine and diethanolamine.

10. The composition of claim 3, wherein the neutralizing agent comprises sodium hydroxide.

11. The composition of claim 1, comprising at least 50 wt % polyisobutylene adhesive.

12. The composition of claim 1, comprising at least 50 wt % hydrophobic synthetic rubber adhesive.

13. The composition of claim 1, wherein the aprotic solvent is selected from the group consisting of dimethylacetamide, N-methylpyrrolidone, dimethylsulfoxide and combinations thereof.

14. The composition of claim 1, wherein the unsaturated fatty acid is a fatty acid with 11 to 21 carbons or a mixture of such fatty acids.

15. The composition of claim 1, wherein the unsaturated fatty acid comprises oleic acid, linoleic acid, or linolenic acid.

16. The composition of claim 1, wherein the alpha-hydroxy acid comprises an acid with 1 to 8 carbons with an alpha-hydroxyl group.

17. The composition of claim 1, wherein the alpha-hydroxy acid is selected from the group consisting of lactic acid, glycolic acid, malic, citric, alpha-hydroxy caprylic acid, alpha-hydroxybutyric acid and combinations thereof.

18. The composition of claim 1, wherein the lipophilic permeation enhancer is present at about 1-20 wt %.

19. The composition of claim 1, wherein the lipophilic permeation enhancer is selected from the group consisting of methyl laurate, propylene glycol monolaurate, glycerol monolaurate, glycerol monooleate, lauryl lactate, myristyl lactate and combinations thereof.

20. The composition of claim 1, wherein the matrix modifier is present at about 4-20 wt % of the composition.

21. The composition of claim 1, wherein the matrix modifier is selected from the group consisting of fumed silica, colloidal silicon dioxide, cross-linked polyvinylpyrrolidone, soluble polyvinylpyrrolidone, a cellulose derivative, polyacrylamide, polyacrylic acid, a polyacrylic acid salt, kaolin, bentonite and combinations thereof.

22. A patch comprising an adhesive matrix made by a process which comprises drying the composition of claim 1.

23. The patch of claim 22, wherein the adhesive matrix after said drying comprises at least 15 wt % liquid.

24. The patch of claim 22, wherein the adhesive matrix after drying has a coat weight between about 10 mg/cm$^2$ and 50 mg/cm$^2$.

25. The patch of claim 22, wherein the in vitro delivery range of tamsulosin is at least 1.7-12.7 µg/cm$^2$ per hr.

26. The patch of claim 22, wherein the adhesive matrix further comprises a nonwoven material.

27. The patch of claim 22, which in use over a 24-hour period of time is non-irritating or no more than mildly irritating.

28. The patch of claim 22, wherein the patch maintains self-adhesion for at least 7 days when it is worn.

29. A method of manufacturing a transdermal drug-in-adhesive patch for delivery of tamsulosin, comprising the steps of (a) dissolving tamsulosin or a pharmaceutically acceptable salt of tamsulosin in an aprotic solvent, (b) combining the tamsulosin solution with a lipophilic permeation enhancer, an optional organic solvent, and an unsaturated fatty acid, (c) adding to the result of (b) a matrix modifier and homogenizing the resulting solution, (d) mixing the result of (c) with a polyisobutylene adhesive or hydrophobic synthetic rubber adhesive in a suitable solvent.

30. The method of claim 29, further comprising adding a neutralizing agent to the result of steps (a) or (b).

31. The method of claim 29, further comprising solvent casting the result of step (d).

32. The method of claim 29, resulting in a weight ratio of tamsulosin to the cast, dried matrix of at least 1 wt %.

33. The method of claim 29, where the aprotic solvent is selected from the group consisting of dimethylacetamide, N-methylpyrrolidone, dimethylsulfoxide and combinations thereof.

34. The method of claim 29, wherein the pharmaceutically acceptable salt of tamsulosin is tamsulosin hydrochloride.

35. A method of treating a urological condition, comprising administering to a patient suffering from or in danger of developing such a condition a transdermal patch comprising a tamsulosin-containing composition of claim 1.

36. A composition for making a patch for the transdermal delivery of an active agent which has poor solubility in an adhesive matrix, the composition comprising (a) at least 1 wt % the active agent or a pharmaceutically acceptable salt of the active agent, (b) at least 40 wt % polyisobutylene adhesive or hydrophobic synthetic rubber adhesive, (c) about 1-20 wt % of an aprotic solvent in which the active agent dissolves readily, (d) about 1-20 wt % of an unsaturated fatty acid or an alpha-hydroxy acid a mixture of unsaturated fatty acids or alpha-hydroxy acids or of both unsaturated fatty acids and alpha-hydroxy acids, (e) a lipophilic permeation enhancer, and (f) a matrix modifier.

37. A transdermal delivery system comprising tamsulosin or a pharmaceutically acceptable salt thereof and an alpha-hydroxy acid, wherein the molar ratio of alpha-hydroxy acid to tamsulosin is at least 0.05:1.

38. A transdermal delivery system comprising tamsulosin or a pharmaceutically acceptable salt thereof and DMSO, wherein the ratio of the cumulative delivery of tamsulosin to cumulative delivery of DMSO is
   at least 0.05 during the period from 72 to 120 hours, and
   at least 0.08 during the period from 120 to 168 hours.

39. The transdermal delivery system of claim 38, wherein the ratio of the cumulative delivery of tamsulosin to the cumulative delivery of DMSO is
   no more than about 0.15 in the first 72 hours,
   no more than about 0.38 in the first 120 hours, and
   no more than about 0.60 in the 168 hour period.

40. The composition of claim 1, wherein at least a portion of the tamsulosin is present in the form of tamsulosin free base.

* * * * *

UNITED STATES PATENT AND TRADEMARK OFFICE
CERTIFICATE OF CORRECTION

| | | |
|---|---|---|
| PATENT NO. | : 8,784,879 B2 | Page 1 of 1 |
| APPLICATION NO. | : 12/687586 | |
| DATED | : July 22, 2014 | |
| INVENTOR(S) | : Singh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 393 days.

Signed and Sealed this
Thirteenth Day of October, 2015

Michelle K. Lee
*Director of the United States Patent and Trademark Office*